US00PP14004P29

(12) United States Plant Patent
Olsthoorn

(10) Patent No.: US PP14,004 P2
(45) Date of Patent: Jul. 22, 2003

(54) SPATHIPHYLLUM PLANT NAMED 'SWEET LAURETTA'

(75) Inventor: Petrus C. M. Olsthoorn, Monster (NL)

(73) Assignee: Pothos Plant B.V., Honselersdijk (NL)

( * ) Notice: Subject to any disclaimer, the term of this patent is extended or adjusted under 35 U.S.C. 154(b) by 0 days.

(21) Appl. No.: 10/076,579

(22) Filed: Feb. 19, 2002

(51) Int. Cl.[7] ..... A01H 5/00
(52) U.S. Cl. ..... Plt./364
(58) Field of Search ..... Plt./364

(56) References Cited

PUBLICATIONS

UPOV–ROM GTITM Computer Database 2002/03, GTI Jouve Retrieval Software, Citation for Spathiphyllum 'Sweet Lauretta'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct Spathiphyllum plant named 'Sweet Lauretta' characterized by having a dark green leaf color, large leaf size, vigorous growth, large white inflorescences and spadix, and long pedicels.

2 Drawing Sheets

Latin name of the genus species of the plant claimed: Spathiphyllum hybrid.

Variety denomination: 'Sweet Lauretta'.

BACKGROUND OF THE INVENTION

The present invention relates to a new and distinct cultivar of Spathiphyllum plant, hereinafter referred to by the name 'Sweet Lauretta'.

The new cultivar originated from a cross made in a controlled breeding program in Monster, The Netherlands. The female parent is '91327-10' (unpatented). The male parent is '93161-95' (unpatented). 'Sweet Lauretta' was discovered and selected by the inventor, Petrus C. M. Olsthoorn, as a flowering plant within the progeny of the stated cross in a controlled environment in Monster, The Netherlands.

Asexual reproduction of the new cultivar was first performed by tissue culture in week 12 of 1998 in Honselersdijk, The Netherlands and has demonstrated that the combination of characteristics as herein disclosed for the new cultivar are firmly fixed and retained through successive generations of asexual reproduction and reproduce true-to-type.

BRIEF DESCRIPTION OF THE INVENTION

The following traits have been repeatedly observed and are determined to be basic characteristics of 'Sweet Lauretta' which in combination distinguish this Spathiphyllum as a new and distinct cultivar:

1. .Dark green leaf color;
2. Big leaf size;
3. Vigorous growth;
4. Large white inflorescences with large spadix; and
5. Long pedicels.

'Sweet Lauretta' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Honselersdijk, The Netherlands, under conditions which closely approximate those generally used in commercial practice.

Of the many commercial cultivars known to the present inventor, the most similar in comparison to 'Sweet Lauretta' is the cultivar 'Cupido' (unpatented). 'Sweet Lauretta' has darker, glossier, longer and wider leaves than 'Cupido'. 'Sweet Lauretta' grows 20 to 30 percent more vigorously than 'Cupido'. The inflorescences of 'Sweet Lauretta' are much larger than those of 'Cupido'. The spadix of the inflorescences of 'Sweet Lauretta' are 30 to 40 percent larger than the spadix of the inflorescences of 'Cupido'. The main vein color of 'Sweet Lauretta' is lighter than the main vein color of 'Cupido'. The inflorescence stem of 'Sweet Lauretta' is darker than the inflorescence stem of 'Cupido'. 'Cupido' is more sensitive to light than 'Sweet Lauretta', resulting faster lighter leaf color. Finally, in order to get the shoots of a Spathiphyllum to flower gibberalic acid is added. 'Cupido' needs more than twice the concentration of this hormone than 'Sweet Lauretta' to get the same result.

BRIEF DESCRIPTION OF THE DRAWINGS

The accompanying photographic drawings show 35-week old plants of 'Sweet Lauretta'.

The first drawing shows a 35-week old plant on the left and a close up of the inflorescence on the right.

The second drawing shows on the upper side a comparison photo of 'Sweet Lauretta' on the left and comparison variety 'Cupido' to the right. The lower comparison photo shows a leaf of 'Cupido' (upper) and 'Sweet Lauretta' (lower).

DETAILED BOTANICAL DESCRIPTION

The following observations, measurements and values describe the new cultivar at 35-weeks as grown in Honselersdijk, The Netherlands under conditions which closely approximate those generally used in commercial practice. Grown in standard glasshouses in well-drained cocos, pH values in cocos/peat soil (50/50) is 6.0–6.2 and 5.8 –6.0 in potting soil. Base fertilizing (PG-mix) is 0.75 kgs in cocos/peat soil as well as in potting soil. This species needs careful fertilizer treatment; mixes of calcium nitrate, iron chelate (EDDHA and DTPA), magnesium sulphate, mono potassium phosphate, potassium nitrate, borax, manganese, molybdenum and copper sulphate. Ideal growing conditions under which this plant is grown is 21–23 degrees Celsius during the day and 20 degrees Celsius at night. For flower initiation 'Sweet Lauretta' gets 80 ppm of gibberalic acid (depending on the pot size, plant development and age of plant).

Color references are made to The Royal Horticultural Society Colour Chart (R.H.S.), except where general colors of ordinary significance are used. Color values were taken under daylight conditions at approximately noon in Boskoop, The Netherlands.

Origin: Honselersdijk, The Netherlands, November 2001.
Parentage:
*Male parent.*—'91327-10'.
*Female parent.*—'93161-95'.
Classification:
*Botanical.*—Spathiphyllum.
*Commercial.*—Spathiphyllum cv. Sweet Lauretta.
Propagation: By tissue culture.
Plant:
*Appearance.*—Upright to broad upright with leaf petioles growing directly from base.
*Height.*—Average 80 cm (excluding inflorescences).
*Width.*—Average 85 cm.
*Growth habit.*—Moderately vigorous to vigorous.
*Time of flowering.*—30 weeks after potting of a 20 cm cutting.
*Winter hardiness.*—USDA Zone 10.
*Stems.*—Leaves grow directly from base, so no stems are visible.
*Roots.*—Time to initiate roots: 1–2 weeks under 21–23 degrees Celsius (day) and 20 degrees Celsius at night. Time to develop roots: 3–4 weeks under 21–23 degrees Celsius (day) and 20 degrees Celsius at night. Rooting habit: Freely branching.
Foliage:
*Shape.*—Narrow elliptic to narrow ovate.
*Apex.*—Apiculate, often curled downwards.
*Base.*—Attenuate.
*Texture.*—Smooth, glossy, somewhat leathery.
*Leaf color.*—Upper surface: Green, closest to but darker in color between RHS 147A and RHS 139A. Lower surface: Green RHS 137B.
*Midrib color.*—Upper Surface: Green RHS 143A. Lower Surface: Yellow-green RHS 144B to RHS 144C.
*Size of leaf.*—Width: Average 14 cm. Length: Average 37 cm. Petiole: Average length 52 cm, average diameter 5 mm, rounded, green darker than but closest in color between RHS 143A and RHS 139A.
*Petiole sheath.*—Average 28 cm long and 5 mm wide (measured at halfway point).
*Geniculum.*—Average length 3.9 cm, average width 6 mm, green in color RHS 143A to RHS 143B.
*Veins.*—Average 14 pairs of furrowed secondary veins, upper side green darker than but closest in color between RHS 147A and RHS 139A, under side color yellow-green RHS 144A to RHS 144B.
Inflorescence description:
*Immature.*—Peduncle: Average length 75 cm, average diameter 5 mm, rounded, green in color RHS 143A to RHS 143B. Spathe: Average length 16 cm, average width 6.5 cm, cupped, average depth 2.2 cm.
*Mature.*—Spathe: Size: Average length 18 cm, average width 6.9 cm, cupped, average depth 2.5 cm. Color: Unopened Bud: White, closest in color between RHS 155A and RHS 157D. Fully Open: Front Surface: White, closest in color between RHS 155A, midrib green-white; RHS 157A. Back Surface: White, closest to RHS 155A, midrib green RHS 143A to RHS 143B Apex: Apiculate, green RHS 143C. Faded: Front Surface: Brown RHS 199A. Back Surface: Brown RHS 199A to RHS 199B. Apex: Brown RHS 199A to RHS 199B.
*Arrangement.*—Solitary.
*Shape.*—Broad-lanceolate; base decurrent.
*Margins.*—Entire.
*Fragrance.*—Sweet, pleasant.
*Lastingness of the individual inflorescence.*—On average over two weeks.
Reproductive organs:
*Spadix.*—Size: Average length 5.8 cm, average width 1.3 cm. Quantity: Average 175 individual flowers per spadix. Pedicel length: 1 to 1.5 cm. Color: Greyed-yellow RHS 160C. Stamens: 6, pressed against styles. Pistil: Each individual flower has one pistil with a tri-parted stigma; the pistil has an average length of 2 mm and is greyed-yellow in color, RHS 160C to RHS 160D.
*Pollen.*—Yellow-white RHS 158A.
Seed production: No observations to date.
Fruit production: No observations to date.
Disease resistance/susceptibility: No observations to date.

I claim:

1. A new and distinct Spathiphyllum plant named 'Sweet Lauretta', substantially as illustrated and described herein.

* * * * *

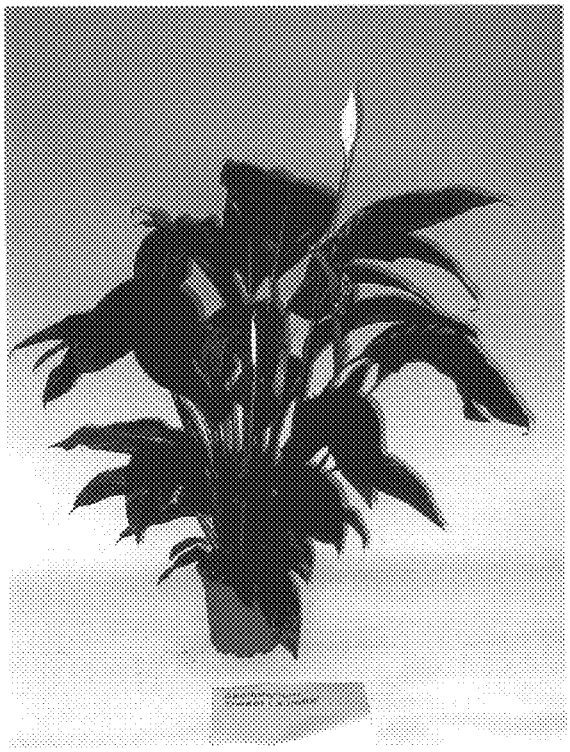
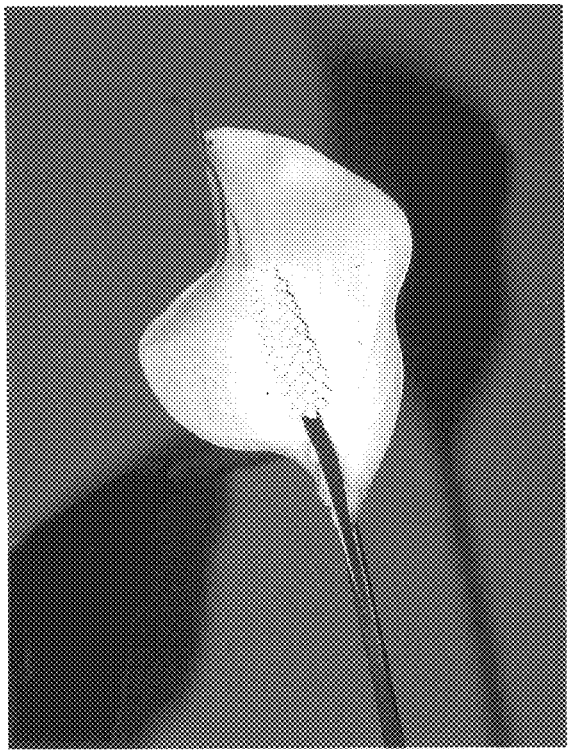

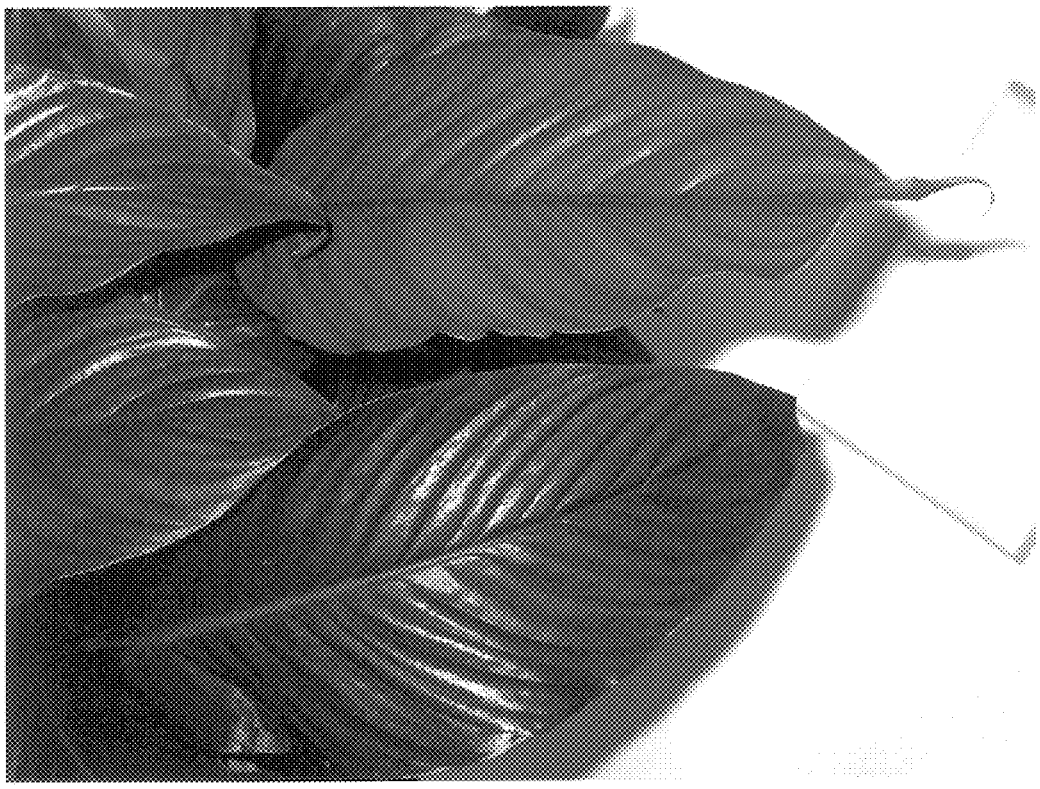

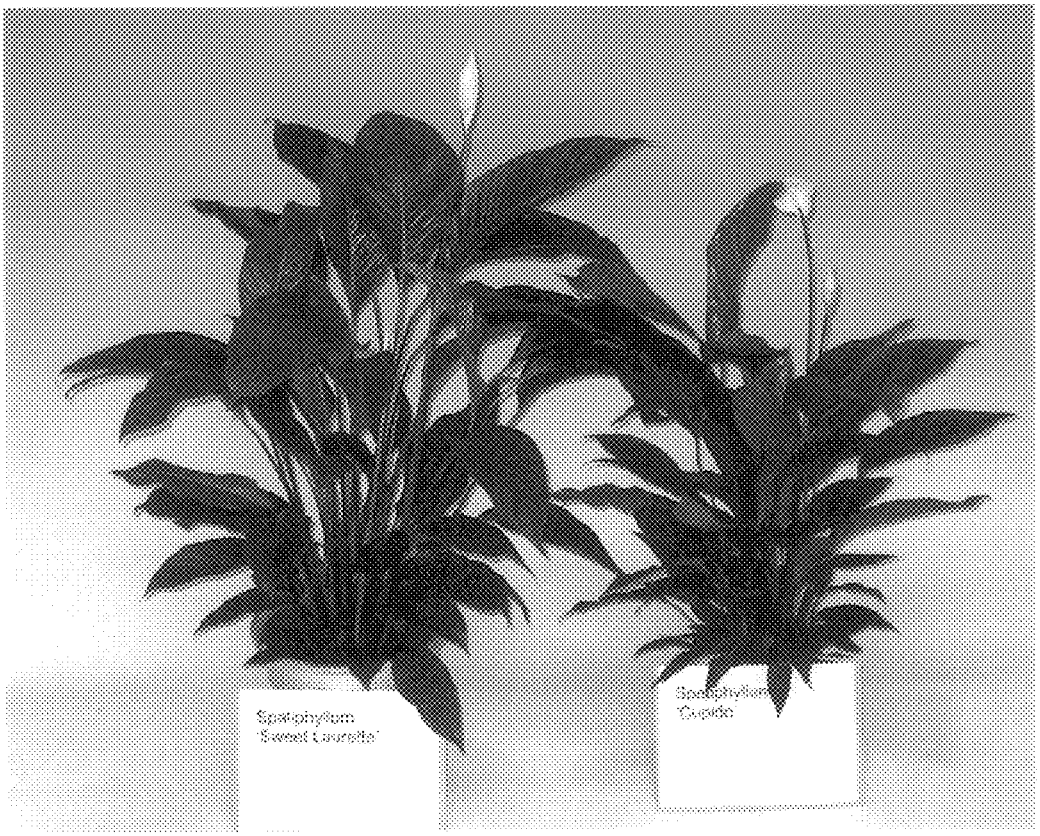
Spathiphyllum
'Sweet Laurette'
Spathiphyllum
'Cupido'